(12) United States Patent
Steg

(10) Patent No.: US 7,811,302 B2
(45) Date of Patent: Oct. 12, 2010

(54) LANCET DEVICE FOR PUNCTURING THE SKIN

(75) Inventor: Henning Steg, Tyresö (SE)

(73) Assignee: Haemedic AB, Tyreso (SE)

( * ) Notice: Subject to any disclaimer, the term of this patent is extended or adjusted under 35 U.S.C. 154(b) by 393 days.

(21) Appl. No.: 11/514,160

(22) Filed: Sep. 1, 2006

(65) Prior Publication Data

US 2007/0244498 A1 Oct. 18, 2007

(30) Foreign Application Priority Data

Apr. 13, 2006 (EP) .................................. 06007800

(51) Int. Cl.
*A61B 17/14* (2006.01)
*A61B 17/32* (2006.01)

(52) U.S. Cl. ........................ 606/181; 606/182; 606/183

(58) Field of Classification Search ................. 606/181, 606/182

See application file for complete search history.

(56) References Cited

U.S. PATENT DOCUMENTS

| 4,653,513 A | 3/1987 | Dombrowski |
| 5,366,469 A * | 11/1994 | Steg et al. .................... 606/182 |
| 5,540,709 A | 7/1996 | Ramel |
| 5,628,765 A * | 5/1997 | Morita ........................ 606/182 |
| 6,322,574 B1 * | 11/2001 | Lloyd et al. .................. 606/181 |
| 6,852,119 B1 | 2/2005 | Abulhaj et al. |

FOREIGN PATENT DOCUMENTS

| EP | 0 565 819 | 10/1993 |
| EP | 0 678 278 | 10/1995 |
| EP | 1 247 489 | 10/2002 |
| WO | WO 2005/094680 | 10/2005 |
| WO | WO 2005/110227 | 11/2005 |

* cited by examiner

*Primary Examiner*—Anhtuan T Nguyen
*Assistant Examiner*—Tin Nguyen
(74) *Attorney, Agent, or Firm*—Bacon & Thomas, PLLC

(57) ABSTRACT

A lancet device for puncturing the skin of mammals, in particular of a human, includes a punch element, a manipulator, and a bushing element for the internal, axially displaceable reception of the punch element. The punch element on its free end has a lancet, provided with a sharp tip, for intentionally entering the skin. The lancet, by means of a force acting in the axial direction on the free end of the bushing via the punch element can be made to enter the skin from the end of the bushing outward with a preadjustable momentum, and a blocking arrangement using an axially slidable sleeve inside the bushing is provided, which, once the lancet has entered the skin, prevents the possibility of a reentry by locking itself within the bushing.

18 Claims, 3 Drawing Sheets

LANCET DEVICE FOR PUNCTURING THE SKIN

A. BACKGROUND

1. Field

The invention relates to a lancet device for puncturing the skin of mammals, in particular humans. The lancet device includes a punch element, provided with a manipulator device, and a bushing element, provided with a grip, for internally receiving the punch element in an axially displaceable relationship. The punch element, on its free end pointing away from the manipulator, carries a lancet provided with a sharp tip for deliberate puncturing of the skin. The lancet, via the punch element, and by means of a force acting in the axial direction on the free end of the bushing, is caused to enter the skin in a direction from the end of the bushing outwardly with a preadjustable force. Blocking means are provided which, once the lancet has entered the skin, prevents the lancet from being able to reenter the skin a second time.

2. Related Art

A lancet device of this kind is known (Published European Patent Application EP A 0 565 819). Many embodiments of lancet devices for puncturing the skin, particularly human skin, have long been known and have long been used with more or less good success for example in outpatient care, medical facilities, hospitals, doctors' offices, Red Cross facilities, disaster shelters, and the like, in order to obtain small quantities of blood for blood tests. The essential prerequisite for these lancet devices is that they must be capable of being produced very economically, since they are often used in great quantities by the above-listed institutions and have to be kept on hand there in large quantities as well, and they are also intended for use in Third World countries.

Another requirement of this lancet device is that at least those parts of the lancet device that directedly punch through human skin, or in other words have direct contact with the human tissue and blood located under the outer skin, must be kept absolutely sterile continuously until the lancet device is used. As a rule, these are the parts of the lancet device that are meant to penetrate the skin tissue to a predetermined depth in order to penetrate blood vessels and cause the blood to leave the entry opening of the wound, namely lancets comprising a steel body of substantially circular cross section that is sharpened on its end pointing toward the skin to be punctured.

Generic lancet devices as described above include blocking means that prevent the lancet device, once it has been used as intended, from being re-used ever again.

Lancet devices that do not have these blocking means can in principle be re-used, but this can lead to major diagnostic mistakes or, much more seriously, to infections of the user of the lancet device from germs from the previous user that were not eliminated.

For the above reasons, the trend is to employ only lancet devices that can in fact be used only once; that is, re-use, even if desired, should always be prevented by mechanical means in the lancet device, especially when it is not possible to preclude re-use of the lancet device by some groups of users. In many countries, regulations exist whereby only single-use lancet devices can be used.

The prior art lancet devices that use mechanical means to allow only a single use of the lancet device are characterized by a comparatively complex construction. While the capabilities of these known lancet devices to be tripped or used only once is typically assured, they do have a major disadvantage, namely that their production costs are considerably higher compared to lancet devices that can be used multiple times. As a result, these lancet devices that can be used only once are not used throughout the groups of users in question, even though it is intrinsically desirable, for both health reasons and health policy reasons, that they be so used by such users.

B. SUMMARY OF THE INVENTION

It is therefore the object of the present invention to create a lancet device of the type described above, that is, a lancet device that is capable of being used only once and does not allow any re-use; which is very simple in construction and can be produced more economically than prior art lancet devices of this type; which assures absolute sterility of the parts of the lancet device that penetrate human skin until just before use; which always assures a uniform entry of the lancet tip into the skin, regardless of the skill or aptitude of the person using it; and which, once the skin has been punctured, assures that the lancet tip is shielded to prevent unintentional and accidental injury to an attendant by infection from blood adhering to the lancet tip.

This object is attained according to the invention in that within the interior of the bushing element, an axially displaceable sleeve element is provided, and the sleeve element has a projection or projections pointing essentially toward the axis. A first projection on the punch element that points away from the axis is slidingly displaceable in such a way relative to the sleeve that it engages the projection axially from behind the sleeve in the course of the entry of the lancet into the skin, and in the course of the retraction of the lancet into the end of the bushing displaces the sleeve element axially in the direction of the punch manipulator.

The advantage of the embodiment according to the invention is essentially that by the structural means provided by the invention, there is no possibility for a user of such a lancet device to trip it or use it again once it has been used once. Because of the structural arrangement of the invention, it is not possible once the lancet device has been used or tripped for a first time, to trip it one more time, since the sleeve element, after tripping, immovably engages the manipulator of the punch element that holds the lancet, and thus the manipulator of the punch element is no longer movable in the axial direction.

In accordance with the objective of the invention, after use of the lancet device, the lancet tip, after reentering the end of the bushing, is shielded and is immovable; that is, the lancet tip cannot be touched either intentionally or accidentally, so that transferring an infection to third parties by blood adhering to the lancet tip is no longer possible.

Finally, the preferred embodiment of the invention is distinguished by a very simple but highly effective construction, since compared to the prior art lancet devices which otherwise are of the same design as the lancet devices of the known type that are capable of repeated use, has only one additional element, namely the sleeve element. The production costs for the lancet device according to the invention are thus only slightly above those for lancet devices of the same design that have no means by which tripping of the lancet device after a first use is prevented.

In accordance with another advantageous feature of the lancet device, the sleeve element, on its end essentially opposite the first projection, has a shoulder which, after the conclusion of the axial displacement in the direction of the punch manipulator, engages a bushing shoulder, provided on the inside of the bushing element, from behind. The locking of the lancet device once it has been used thus occurs in the final analysis between the sleeve element and the bushing element. The sleeve thus is axially displaced in the retraction direction of the lancet into the bushing element far enough so that the shoulder of the sleeve element engages the bushing shoulder from behind. In the process, the sleeve element comes to rest on the inside of the grip device of the bushing, so that the manipulator of the punch element is no longer movable.

A number of possible construction options provide assurance that after the conclusion of the axial displacement in the direction of the manipulator, the sleeve element will engage the bushing shoulder provided on the inside of the bushing element from behind. The illustrated embodiment advantageously provides that the sleeve element, at least in the region of its shoulder, is prestressed radially away from the lancet device axis. This can be accomplished, for instance, by providing that the sleeve element, during the production process, is radially dimensioned such that, due to its elastic deformability, it is slightly compressed radially, or in other words, its diameter is compressed, by the interior of the bushing element in the course of assembly as it is introduced into the bushing interior. The self-actuation resulting from the elastic restoration of the sleeve element is then utilized, so that the sleeve element first engages at least partly the inner wall of the bushing element, and after the aforementioned axial displacement, increases in size radially outward again and thus engages the bushing shoulder from behind.

In accordance with still another advantageous feature of the lancet device according to the invention, the punch element, at its free end, has a cap element which in sterile fashion sheathes the lancet tip protruding from that end, such that only just before use of the lancet device does the cap element have to be removed from the lancet tip, whereby the cap element of the lancet tip is kept sterile for an unlimited length of time.

In accordance with still another advantageous feature of the lancet device of the invention, the punch element and the cap element may be formed as an integral, one-piece molded part, with the result that this feature can be produced in a single operation and hence economically.

To make possible the removal of the cap element quickly and easily from the punch element and to thus expose the lancet tip for the puncturing operation using the lancet device, the punch element, in the region of the connection with the cap element, is preferably provided with a weakened breaking zone. The breaking zone permits fast removal of the cap element, preferably where the breaking zone is advantageously formed by radially tapering an area of the connection region, so that the cap element merely needs to be rotated relative to the punch element slightly by an angle α for its removal, thereby breaking the connection between the punch element and the cap element, or in other words breaking the taper area of the connection region.

To prevent the lancet device from being tripped unintentionally in the unused state, in accordance with another advantageous feature, the cap element, on its end that in the untripped state of the lancet device is positioned within the bushing element, has essentially two locking ribs protruding essentially radially from the cap element, and which, upon movement of the punch manipulator in the axial direction, strike an abutment provided in a region at the free end of the bushing element. Thus as long as the cap is covering or enclosing the lancet tip in sterile fashion, it is impossible to trip the lancet device unintentionally.

Preferably, upon rotation of the cap element about an axis by an angle α, the locking ribs are located so they face an abutment-free portion in the region at the free end of the bushing element, and because of the rotation of the cap element about the angle α, the cap element being grasped with the thumb and index finger of a user during the rotation process, the connection between the cap element and the punch element is broken, and the cap element can then be pulled out of the bushing element.

Advantageously, the punch element has a second punch element projection, which extends away from the axis of the lancet device and is located downstream, in terms of the direction of projection of the lancet, of the first punch element projection and spaced apart axially from it, whereby contact of the second projection with a shoulder of the bushing element limits the axial displacement travel of the lancet into the bushing element opposite to the projection direction. Thus after the lancet device has been used, the lancet, traversing a defined reverse travel distance, can be received securely in the bushing element again, sufficiently deep inside it to assure that the tip of the lancet can no longer be touched, even accidentally.

As already noted at the outset, the means which cooperate with the manipulator of the punch element for generating a force which drives the lancet when the lancet device is tripped so the lancet enters the skin of a subject, can be different in terms of construction. However, it is particularly advantageous to embody the manipulator of the punch element at least partially as an elastic spring body resembling a diaphragm, which causes the lancet, via motion of the punch element after an adjustable pressure point of the diaphragm has been overcome, to enter the skin with a predeterminable momentum. As a result, in a structurally simple way, the tripping of a puncturing operation with the lancet device of the invention is accomplished entirely regardless of the individual skill or aptitude of the person or persons using the lancet device, or in other words free of variables that could affect this operation, since the user has to make sure only to overcome the pressure point of the spring diaphragm of the punch element manipulator. Once the pressure point is overcome, the momentum with which the lancet tip, carried by the punch element, moves ahead and penetrates the skin of a subject to a predeterminable depth is determined exclusively by the spring constant of the diaphragm.

Preferably, the diaphragm is embodied as a substantially disc-like body, which is curved in concave fashion in cross section; the concave curvature in the unused state of the lancet device is configured such that it curves away from the bushing element in an axial direction.

Although it is fundamentally possible for the diaphragm to be embodied and produced in any arbitrary suitable way, it is nevertheless advantageous to construct the diaphragm and the shaftlike punch element as a one-piece, integrally molded part, so that in principle the lancet device comprises only the punch element with the diaphragm, the bushing element in which the punch element is received, and the sleeve element, along with the metal lancet.

In accordance with the objective of the invention, the lancet device of the invention should be capable of being produced as economically as possible, to make it as widely usable as possible and even to reach users for whom the possibility of using the lancet devices of the generic type has remained closed until now. From this standpoint, it is extraordinarily advantageous to provide both the grip device of the bushing element and the manipulator of the punch element with a disc-like structure and to make a connection between the manipulator and grip via mutual engagement means formed on them. Accordingly, structurally complex connecting means are not needed; instead, the manipulator and grip parts, which jointly form the actual grip of the lancet device, can be connected in the above-described simple way without having to provide additional connecting means, locking means, or adhesive means.

The diaphragm, which is pressed in the direction of the lancet tip by the user, for instance by pressing on the diaphragm with the user's thumb, is deformed elastically until the preset pressure point is reached and in this deformation a slight increase in diameter or generally an increase in external dimensions of the diaphragm results, and in order not to hinder this, which has an adverse effect on the lancet reaching the desired momentum of a predetermined magnitude, the engagement means on the grip of the bushing element is configured in the form of a circumferentially extending groove, and the engagement means on the manipulator of the punch element is formed as a circumferential spring. For connecting the two manipulator and grip sections, the spring engages the groove; however, the connection between the manipulator and grip, that is, the engagement of the spring with the groove, nevertheless allows a slight radial play, so that the aforementioned increase in diameter or radial dimension of the diaphragm until the pressure point is reached can proceed without decreasing the momentum given to the lancet upon tripping.

Finally, it is advantageous to make the punch element, the bushing element, and the sleeve element of plastic, such as injection-moldable plastic such as polypropylene.

Optionally, it may be advantageous to form the sleeve element of some injection-moldable plastic material different from that of the punch element and that of the bushing element, so that if needed the specific desired elastic deformability of the sleeve element in the radial direction can be more suitably accommodated.

C. DESCRIPTION OF THE DRAWINGS

The invention will now be described in detail in terms of an exemplary embodiment, in conjunction with the schematic drawings that follow. In the drawings:

FIG. 1, essentially in section, shows a lancet device which is in an untripped state of rest;

FIG. 2 is a side view of a detail of FIG. 1;

FIG. 3, essentially in section, shows the lancet device in the tripped state, in which the lancet tip has penetrated the skin;

Figure 6:
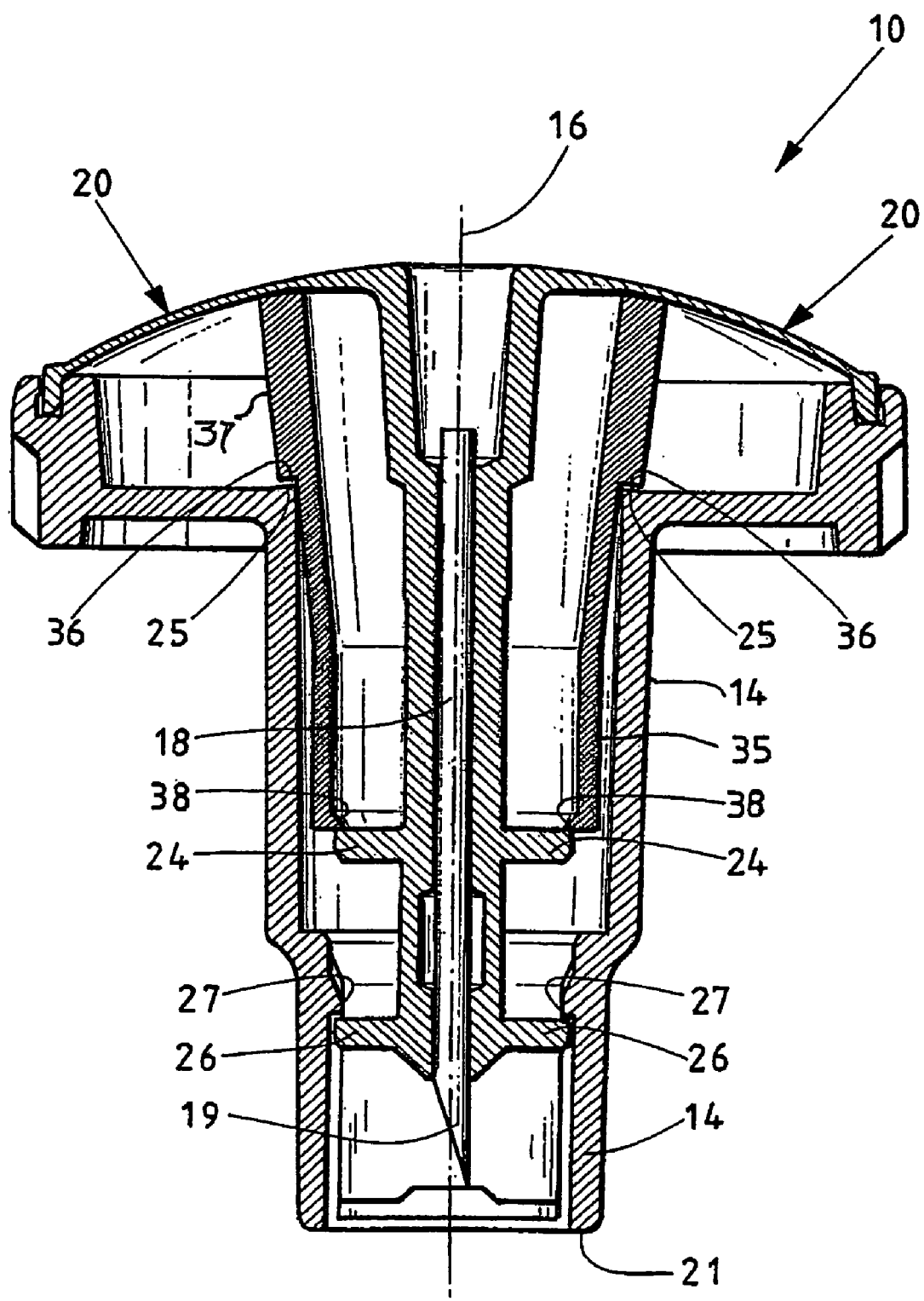

FIG. 6, essentially in section, shows the lancet device after it has been tripped once, in the locked state with the lancet tip retracted into the bushing element.

D. DETAILED DESCRIPTION OF THE PREFERRED EMBODIMENTS OF THE INVENTION

Figure 1:
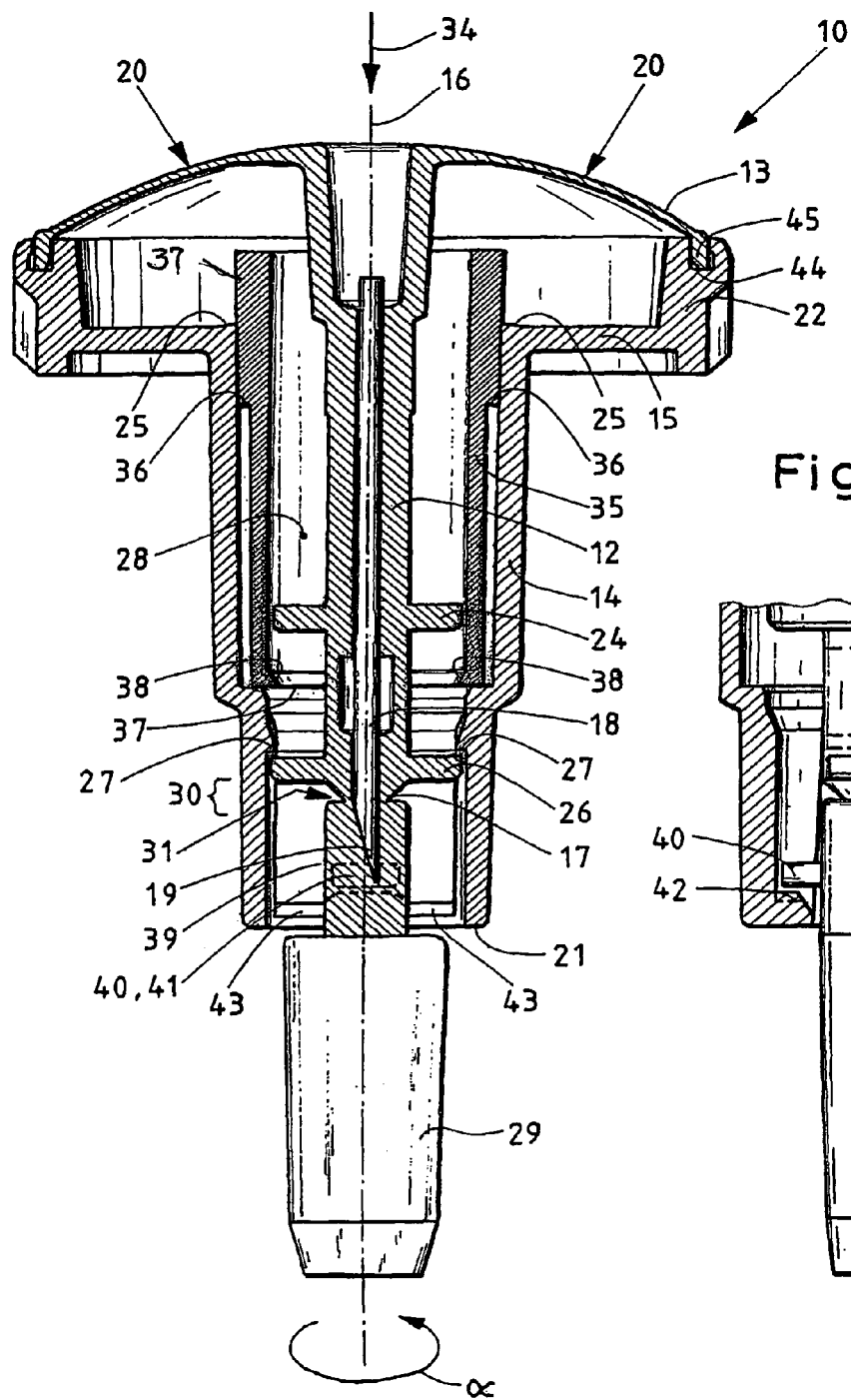

Turning first to FIG. 1, the basic construction of the lancet device 10 will now be described.

The lancet device 10 substantially comprises a bushing element 14, which may have a substantially circular cross section, but it may also for instance have an oval or elliptical cross section. The bushing element 14 has an interior 28. Located in the interior 28 of the bushing element 14 is a sleeve element 35, which, if the interior cross section of the bushing element is circular, also has a substantially circular cross construction. The sleeve element 35 is axially displaceable back and forth in the direction of the arrow 34 and in the opposite direction, in the interior 28 along a central axis 16 that passes through the lancet device 10. A punch element 12 is received centrally along the axis 16 within the bushing element 14 and is likewise movable in the direction of the arrow 34 and in the opposite direction in the interior 28. Centrally relative to the axis 16, a lancet 18 is received in the punch element 12. The lancet 18 has a sharp end 19, hereinafter called the lancet tip, with which the lancet 18 penetrates the skin 11 of a mammal, in particular a human being, to an intended depth, given the intended use of the lancet device 10 (see FIG. 3).

The bushing element 14 is provided with a grip portion 15, which may be embodied essentially as a disc-like form. The grip 15 has an outer upstanding peripheral edge 22, on the vertical upper end of which (as viewed in the drawings) an engagement means is provided, in the form of a groove 44 that likewise essentially extends all the way around the grip 15. The grip 15 is thus embodied essentially as a flangelike element, which protrudes radially away from the bushing element and on the outer edge of which the aforementioned edge 22 is provided.

In the interior 28, above the region of the grip 15 of bushing element 14 that borders on the sleeve element 35, a first bushing extension or shoulder 25 is provided, which given the circular cross section of the bushing element 14 can be regarded as encompassing the top edge of the bushing element 14.

Toward its free end 21, the bushing element 14 is configured in open fashion and in its lower area (as viewed in the drawings) it has a second bushing shoulder 27, which for a bushing element 14 formed with a circular cross section will also be configured to extend all the way around circularly in the interior 28. The function of the first bushing shoulder 25 and a second bushing shoulder 27 will be described hereinafter, in conjunction with the description of the cooperation between the various elements of the punch element 12.

The punch element 12 has a manipulator 13, embodied as a spring diaphragm 20, and a substantially cylindrical, shaftlike body which is received axially centrally 16 in the interior 28 of the bushing element 14. The manipulator 13, embodied as a spring diaphragm 20, of the punch element 12 has a substantially disc-like cross section, and at its peripheral region, encompassing it, an engagement means 45 in the form of a spring portion 45 is provided. The spring portion 45 of the manipulator 13 of the punch element 12 engages the groove 44 in the grip 15 of the bushing element 14. The groove 44 and the spring portion 45 are dimensioned such that the connection of the manipulator and grip 13, 15 (FIG. 1) enables the lancet device 10 to be completely assembled from the individual elements described with a slight radial play in the assembled state. The necessity for the slight radial play will be described in detail hereinafter, in conjunction with the description of the function of the lancet device 10, particularly taking into account the view shown in FIG. 3.

The punch element 12 has a first radial projection 24, essentially radially encompassing the punch element, and a second radial projection 26, protruding radially away from the axis 16 in finlike fashion. The projections 24, 26 are spaced apart axially and are essentially parallel to one another. The first projection 24 is located in the region of the sleeve element 35 in the interior 28, while conversely the second projection 26 is located in the lower part, as viewed in the drawings, of the bushing element 14 and oriented toward the free end 21 of the bushing element. When the punch element 12 moves counter to the direction of the arrow 34, the second projection 26 comes to rest on the second bushing projection 27; that is, the capability of the punch element 12 to move counter to the direction of the arrow 34 is limited by the bushing projection 27.

Figure 2:
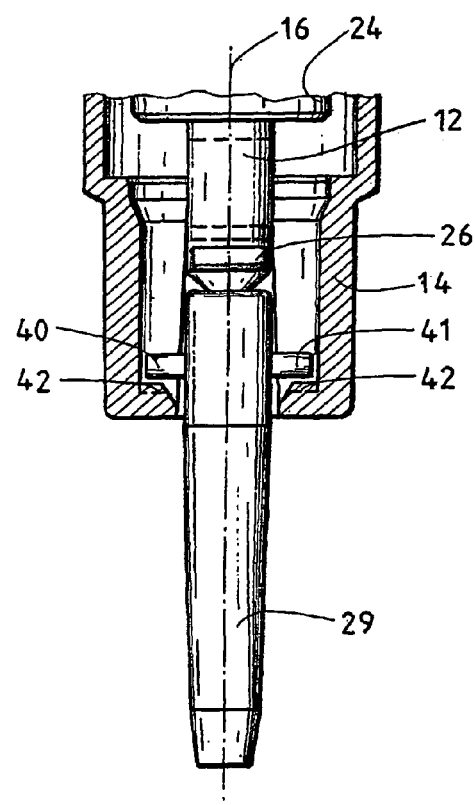

The spring diaphragm 20 and the shaftlike punch element 12 are formed integrally as a single piece. On its free end 17, the punch element 12 is provided with a cap element 29. The cap element 29 (see FIGS. 1 and 2) in the unused state of the lancet device 10 protrudes out of the free, open end 21 of the bushing element 14. The cap element 29 is designed such that it can be grasped by the user of the lancet device 10, for instance between a thumb and index finger. The cap element 29 sheathes the lancet tip 19 in sterile fashion; that is, during the production process of the punch element 12, the lancet 18 is hermetically sheathed by the material forming the punch element 12 and in its extension in the form of the cap element 29, so that the lancet tip 19 is sheathed in sterile fashion once the production process is concluded. The punch element 12 and the cap element 29 may be embodied as a one-piece molded part. In the region of the connection 30 of the cap element 29, a designated weakened breaking zone 31 is provided. The weakened breaking zone 31 is formed by a radial taper of the connection region 30 (see particularly FIG. 1).

The cap element 29, on its end 39 that is positioned within the bushing element 14 in the untripped state of the lancet device 10, furthermore has two locking ribs 40, 41 that protrude substantially radially from the cap element 29. On the end 21 of the bushing element 14, two abutments 42 protruding radially relative to the direction of the axis 16 are provided (see particularly FIG. 2). In the untripped state of the lancet device 10, if the manipulator 13 is actuated in the direction of the arrow 34, the locking ribs 40, 41 will abut against the abutment 42, preventing the lancet tip 19 from emerging from the free end 21 of the bushing element 14. In other words, whenever the punch element 12 connected to the cap element 29 is positioned in the bushing element 14, actuation or tripping of the lancet device 10 is not possible, since the locking ribs 40, 41 rest on the abutment 42, and thus an axial motion of the punch element 12 in the direction of the arrow 34 is not possible.

Upon rotation of the cap element 29 about the axis 16 by an angle α which may for instance be 90° (see also FIG. 1) the locking ribs 40, 41 reach an abutment-free portion 43 (see FIGS. 1 and 2) in the region of the free end 21 of the bushing element 14. In the course of the rotation of the cap element 29 about the angle α, a physical disconnection occurs between the punch element 12 and the cap element 29, because of the intended breakage of the connection at the weakened breaking zone 31. Counter to a slight force to be exerted in the direction of the arrow 34, the cap element 29 can now, since the locking ribs 40, 41 are located facing the abutment-free portion 43, be pulled out of the free end 21 of the bushing element. In the process, the sharp end 19 of the lancet 18 is then also exposed, and the lancet device 10 is ready to function, or is ready for operation.

To trip the lancet device 10, a force is exerted on the diaphragm 20 of manipulator 13 in the direction of the arrow 34, for instance with the thumb of a user pressing against the diaphragm 20, the grip 15 of the bushing element 14 being grasped between two fingers. Since the diaphragm 20 is embodied in the form of a resilient spring body, the lancet 18, which is now exposed with its lancet tip 19, will be driven to penetrate the skin 11 with a predeterminable momentum (see FIG. 3) to a predetermined depth, via the punch element 12 joined in one piece to the diaphragm 20, once a pressure point that can be adjusted by the configuration of the diaphragm has been overcome. The motion of the diaphragm 20 in the direction of the arrow 34 is limited by its coming into contact with the sleeve element 35. By a suitable choice of the construction of the diaphragm 20, of the sleeve element 35, and of the bushing element 14, the depth to which the diaphragm tip penetrates the skin 11 can be predetermined in a defined way.

Figure 3:
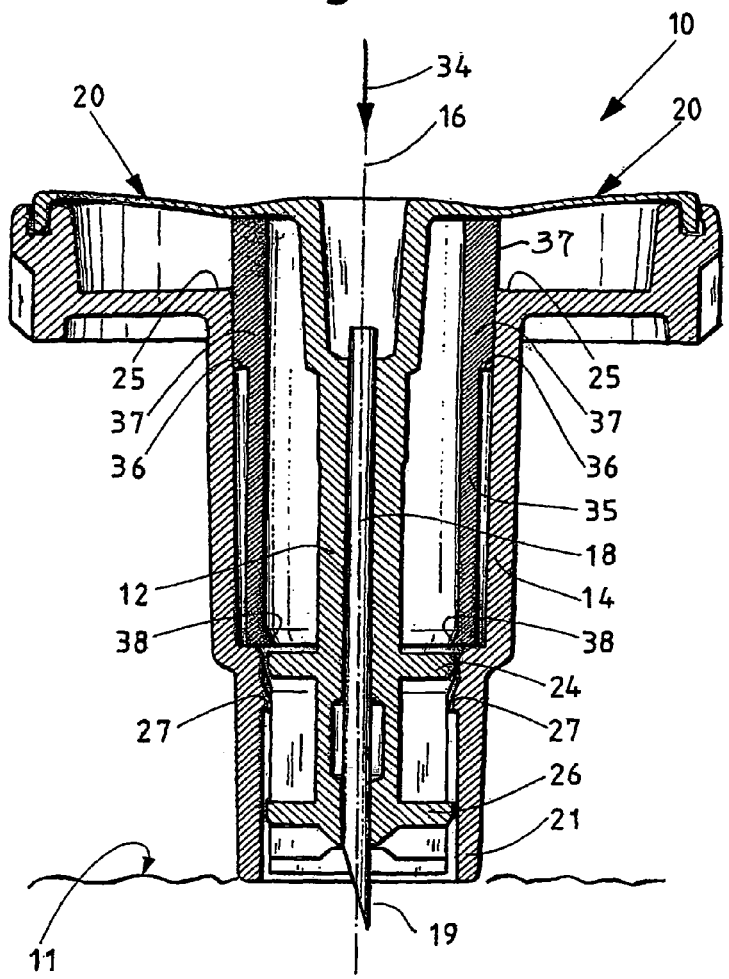
Figure 5:
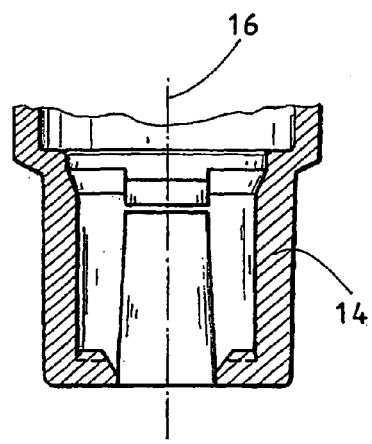
FIG. 5 is a side view of a detail of FIG. 3.
Figure 4:
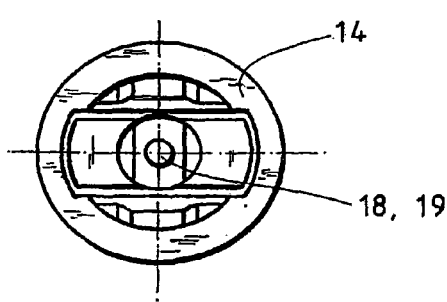
FIG. 4 is a view of the lancet device of FIG. 3 from below.

In the course of the motion of the punch element 12 in the direction of the arrow 34, the first projection 24 of the punch element 12, as shown in the drawings, has slid over the projection or projections 38, provided on the lower end of the sleeve element 35 and now comes to rest axially below the projection 38 (see FIG. 3, which shows the displaced state of the punch element 12).

If the diaphragm 20, after the conclusion of the puncturing operation, is now let go, then because of the intrinsic, intentionally set prestressing of the diaphragm 20, an axial motion of the diaphragm 20 counter to the direction of the arrow 34 ensues, since the diaphragm 20 seeks to resume its untripped basic state (see FIGS. 1 and 6). In the course of this reverse motion of the punch element 12 counter to the direction of the arrow 34, the projection 24 of the punch element 12 likewise presses the sleeve element 35 in the opposite direction from the arrow 34, or in other words upward as shown in the drawings, until the diaphragm 20 has regained its relaxed basic position (see FIG. 6).

The sleeve element 35, on its end 37 essentially opposite the first projection 38, has a second projection 37 above shoulder 36, which after the conclusion of the axial displacement in the opposite direction of the arrow 34 engages the bushing shoulder 25 mentioned above formed on the bushing element 14 from behind or above, so that the axial position of the sleeve element 35 is as shown in FIG. 6. Since the bushing shoulder 25 is now in engagement with the shoulder 36 of the sleeve element 35, and because of the radially outward prestressing of the sleeve element 35, there is no possibility of escaping from this interengaged position. Thus, the blocking state sought according to the invention after a single use of the lancet device 10 is obtained, since by the contact of the sleeve element 35 with the inside of the diaphragm 20, no further motion of the diaphragm 20 in the direction of the arrow 34 again is possible.

The punch element 12, the bushing element 14, and the sleeve element 35 can be produced of suitable, injection-moldable plastic material, such as polypropylene. In principle, however, still other injection-moldable plastic materials are possible for making these elements, and it is also possible for the individual elements listed above of the lancet device 10 to be made from different, suitable plastic materials, for instance in order to be able to better take into account predetermined elastic deformation criteria, for instance of the sleeve element. The lancet 18 itself typically comprises a suitable steel alloy and is embedded in the punch element 12 in the course of the production process of the punch element, in other words in the course of its injection molding.

List of Reference Numerals

10 Lancet device
11 Skin
12 Punch
13 Punch Manipulator
14 Bushing
15 Bushing grip
16 Lancet device longitudinal axis
17 Free end of the punch element
18 Lancet
19 Lancet tip
20 Diaphragm of manipulator
21 Periphery of the diaphragm
22 Rim
23
24 First projection of punch element
25 First Bushing shoulder
26 Second projection of punch element
27 Second Bushing shoulder
28 Interior of bushing
29 Cap
30 Connection
31 Weakened breaking zone
32
33
34 Lancet Exit direction
35 Sleeve
36 Sleeve Shoulder
37 Sleeve end 38 Sleeve projection
39 End of cap
40 Locking rib
41 Locking rib
42 Abutment
43 Abutment-free portion
44 Groove
45 Spring

The invention claimed is:

1. A lancet device (10) for puncturing the skin (11) of mammals, comprising:
   a punch element (12);
   a manipulator (13) operably connected to the punch element;
   a bushing element (14) having a grip (15) and an interior (28) in which the punch element (12) is axially displaceably disposed;
   the punch element (12) having a lancet (18) provided with a sharp tip (19) for deliberate entering of the skin (11) on a free end (17) thereof pointing away from the manipulator (13), wherein, by means of a force acting in a lancing direction along a longitudinal axis (16), away from the manipulator (13), the lancet (18), via the punch element (12), can be made to extend outward from a free end (21) of the bushing to enter the skin (11) with a preadjustable momentum; and
   including blocking means which prevents the possibility of reentry of the lancet (18) into the skin (11) once the lancet (18) has previously entered the skin (11), said blocking means comprising:
   a sleeve element (35) disposed in an axially slidable relationship in the interior (28) of the bushing element (14), and which includes a first sleeve projection (38), oriented radially inwardly towards the longitudinal axis (16),
   wherein a first punch projection (24) defined on the punch element and oriented radially outwardly from the longitudinal axis (16) slidingly passes and locks beyond the first sleeve projection (38) during entry of the lancet (18) into the skin (11) and upon reentry of the lancet (18) into the end (21) of the bushing, the first punch projection (24) engages the first sleeve projection (38) to axially displace the sleeve element (35) in the axial direction (34) towards the manipulator (13).

2. The lancet device as defined by claim 1, wherein the sleeve element (35), on its end (37) opposite the first projection (38), has a shoulder (36), which after the conclusion of the axial displacement in the direction of the manipulator (13) engages a bushing shoulder (25), formed on the bushing element (14), from behind.

3. The lancet device as defined by claim 2, wherein the sleeve element (35), at least in the region of its shoulder (36), is prestressed radially away from the longitudinal axis (16).

4. The lancet device as defined by claim 1, wherein the punch element (12), on a free end (17) thereof, has a cap element (29) which in sterile fashion sheathes the sharp tip (19) protruding from the punch element at that end.

5. The lancet device as defined by claim 4, wherein the punch element (12) and the cap element (29) are formed as a one-piece molded part.

6. The lancet device as defined by claim 4, wherein the cap element (29) has at least two locking ribs (40, 41) on an end (39) that is positioned in the bushing element (14) in the untripped state of the lancet device (10), the at least two locking ribs (40, 41) protruding generally radially from the cap element (29), wherein in the untripped state of the lancet device (10), upon actuation of the manipulator (13) in the axial direction (34), the at least two locking ribs (40, 41) strike an abutment (42) formed in the region of the free end (21) of the bushing element (14).

7. The lancet device as defined by claim 6, wherein upon rotation of the cap element (29) about the longitudinal axis (16) by an angle α, the locking ribs (40, 41) are located facing an abutment-free portion (43) in the region of the free end (21) of the bushing element (14).

8. The lancet device as defined by claim 7, wherein upon rotation of the cap element (29) about the longitudinal axis (16) by an angle α, the integral connection between the cap element (29) and the punch element (12) is broken, and the cap element (29) is removable from out of the bushing element (14).

9. The lancet device as defined by claim 1, wherein the punch element, in the region of the connection with a cap element (29), is provided with a weakened breaking zone (31).

10. The lancet device as defined by claim 9, wherein the weakened breaking zone (31) is formed by a radial tapering of the connection region (30).

11. The lancet device as defined by claim 1, wherein the punch element (12) has a second punch projection (26), which points away from the longitudinal axis (16) and is located downstream, in terms of the exit direction (34) of the lancet (18), from the first punch projection (24) and spaced apart axially from the first punch projection, and which, by coming into contact with a first shoulder (27) of the bushing element (14), limits the axial (16) displacement travel of the lancet (18) into the bushing element (14) counter to the exit direction (34).

12. The lancet device as defined by claim 1, wherein the manipulator (13) of the punch element (12) is formed at least partially as a resilient spring body in the form of a diaphragm (20), which causes the lancet (18), via the punch element (12) after an adjustable pressure point of the diaphragm has been overcome, to enter the skin (11) with a predeterminable momentum.

13. The lancet device as defined by claim 12, wherein the diaphragm (20) is formed as a substantially disc-like body, which is curved in upwardly convex fashion in cross section.

14. The lancet device as defined by claim 12, wherein the diaphragm (20) and the shaftlike punch element (12) are formed integrally as one piece.

15. The lancet device as defined by claim 1, wherein the grip (15) of the bushing element (14) and the manipulator (13) of the punch element (12) each have a substantially disc-like structure and are connectable to each another in the course of the connection of the manipulator (13) and grip (15) via mutual engagement means (44, 45) provided on each of them.

16. The lancet device as defined by claim 15, wherein the engagement means (44) on the grip (15) of the bushing element (14) is formed as a substantially peripheral groove, and the engagement means (45) on the manipulator (13) of the punch element (12) is formed as a substantially peripheral spring, and for connecting the two manipulator and grip (13, 15), the spring engages the groove.

17. The lancet device as defined by claim 1, wherein the connection of the manipulator (13) and grip (15) has a radial play.

18. The lancet device as defined by claim 1, wherein the punch element (12), the bushing element (14), and the sleeve element (35) comprise plastic material.

* * * * *